(12) United States Patent
Meconi et al.

(10) Patent No.: US 6,521,250 B2
(45) Date of Patent: Feb. 18, 2003

(54) TRANSDERMAL THERAPEUTIC SYSTEM CONTAINING ESTRADIOL

(75) Inventors: Reinhold Meconi, Neuwied; Frank Seibertz, Bad Hönningen/Ariendorf; Michael Horstmann, Neuwied; Rainer Lichtenberger, Darmstadt, all of (DE)

(73) Assignees: LTS Lohmann Therapie-Systeme GmbH, Neuwied (DE); Merck Patent GmbH, Darmstadt (DE)

( * ) Notice: Subject to any disclaimer, the term of this patent is extended or adjusted under 35 U.S.C. 154(b) by 0 days.

(21) Appl. No.: 09/522,925

(22) Filed: Mar. 10, 2000

(65) Prior Publication Data

US 2002/0012691 A1 Jan. 31, 2002

Related U.S. Application Data

(63) Continuation of application No. 08/961,039, filed on Oct. 30, 1997, which is a continuation-in-part of application No. 08/545,703, filed as application No. PCT/EP94/01279 on Apr. 25, 1994, now abandoned.

(30) Foreign Application Priority Data

May 6, 1993 (DE) ............................................ 43 14 970
Oct. 27, 1993 (DE) ............................................ 43 36 557

(51) Int. Cl.⁷ ............................ A61F 13/00; A61K 9/70
(52) U.S. Cl. ........................ 424/443; 424/448; 424/449
(58) Field of Search .................... 424/443, 448, 424/449

(56) References Cited

U.S. PATENT DOCUMENTS

| | | | |
|---|---|---|---|
| 4,379,454 A | 4/1983 | Campbell et al. ........... 604/897 |
| 4,624,665 A | 11/1986 | Nuwayser ................. 604/307 |
| 4,668,232 A * | 5/1987 | Cordes et al. .............. 604/897 |
| 5,306,503 A * | 4/1994 | Muller et al. ............... 424/449 |
| 5,393,529 A * | 2/1995 | Hoffmann et al. .......... 424/445 |
| 5,928,666 A * | 7/1999 | Farinas et al. ............. 424/449 |

FOREIGN PATENT DOCUMENTS

| | | |
|---|---|---|
| DE | 2 006 969 | 10/1970 |
| DE | 3 810 896 | 10/1988 |
| DE | 3 205 258 | 2/1991 |
| DE | 3 743 946 | 6/1991 |
| DE | 4 223 360 | 4/1993 |
| EP | 0 072 251 | 2/1983 |
| EP | 0 186 019 | 7/1986 |
| EP | 0 275 716 | 7/1988 |
| EP | 0 285 563 | 10/1988 |
| EP | 0 328 806 | 8/1989 |
| EP | 0 421 454 | 4/1991 |
| EP | 0 483 370 | 5/1992 |
| EP | 0 607 434 | 7/1994 |
| WO | 87/07138 | 12/1987 |

OTHER PUBLICATIONS

Friend et al., Journal of Controlled Release, vol. 7 (1988) pp. 243–250.

Friend et al., Journal of Controlled Release, vol. 9 (1989) pp. 33–41.

* cited by examiner

*Primary Examiner*—Thurman K. Page
*Assistant Examiner*—S. Howard
(74) *Attorney, Agent, or Firm*—Wenderoth, Lind & Ponack, L.L.P.

(57) ABSTRACT

An active-substance-containing transdermal therapeutic system for the controlled release of estradiol or its pharmaceutically acceptable able derivatives alone or combined with gestagens consisting of a layer, an active-substance-containing reservoir which is bonded thereto and produced by using pressure sensitive adhesives, and a removable protective layer is characterized by the fact that the pressure sensitive adhesive comprises esters of colophony.

24 Claims, No Drawings

TRANSDERMAL THERAPEUTIC SYSTEM CONTAINING ESTRADIOL

This application is a continuation of application Ser. No. 08/961,039, filed Oct. 30, 1997, which application is a continuation of now abandoned application Ser. No. 08/545,703, filed Feb. 12, 1996, which application is a national stage application of International Application No. PCT/EP94/01279, filed Apr. 25, 1994.

BACKGROUND OF THE INVENTION

The present invention relates to a transdermal therapeutic system for the controlled release of estradiol or its pharmaceutically acceptable derivatives alone or combined with gestagens, such as levonorgestrel, to human or animal skin. The present invention further relates to the use and to a process for the production of this system.

In the therapy of various diseases, transdermal therapeutic systems (TTS) have been introduced on the market. Also, transdermal therapeutic systems containing the estrogenic active substance 17-β-estradiol used as therapeutic agent for climacteric complaints and—for some time now—against osteoporosis are commercially available and show good therapeutic results.

Levonorgestrel is a synthetic gestagen derivative which has mainly been used in contraceptives in combination with orally effective estrogens. In such preparations gestagens, consequently including levonorgestrel, have the function to cause a "physiologic" abstraction hemorrhage which is as short and rapid as possible by means of an adequate trophic premedication of the uterus. There are also hints that the gestagen addition has a protective effect against the risk of endometrial tumors.

For this reason, it is appropriate to use a cyclic treatment also for the indication of postmenopausal complaints, i.e., to make use of a temporary fixed drug combination consisting of estrogens (e.g., estradiol) and gestagens (e.g., levonorgestrel). A combination of the two active substances in a common, monolithic transdermal therapeutic system which would have to be applied only once a day or even once to twice a week is particularly interesting. Owing to its high efficiency and permeativity through the skin levonorgestrel is excellently suitable for such a system.

Experimental systems for the transdermal delivery of levonorgestrel are described in literature (Friend et. al., J. Controlled Release 7, 243–250 (1988)). However, according to this estimation, permeation improvers (enhancers), e.g., alkyl esters of short-chain fatty acids, are required for the successful transdermal therapy with sufficiently small system surfaces (Friend et. al., J. Controlled Release 9, p. 33–40 (1989)).

Numerous devices for the transdermal application of estrogens and gestagens have been disclosed. Nakagawa et al. (EP-A 0 483 370) obtained a matrix-type transdermal therapeutic system for estradiol alone by using styrene-isoprene block copolymer, moisture-absorbing polymer domains, and the enhancer (and antipruritic agent) crotamiton. Another conception is the simultaneous application of estradiol and an enhancer (ethanol) in a membrane-controlled reservoir system (Campbell et al., U.S. Pat. No. 4,379,454); this can also be used in a combined administration form comprising the gestagen norethisterone acetate (Frankhauser and Schenkel, DE 3 810 896).

However, transdermal therapeutic systems for the release of estradiol and/or gestagens have the disadvantage that they either contain ethanol or that they exhibit the potential danger of the active substance being recrystallized in the course of time.

It is known from DE-OS 32 05 258 and EP 0 285 563 to administer estradiol and ethanol simultaneously in a patch formulation. However, the production of this patch is very expensive, and the wearing comfort after application is low because of missing flexibility.

EP 0 285 563 describes a transdermal therapeutic system for the combined application of estrogens and gestagens. The reservoir has the active substance formulation, optionally a membrane, and ethanol as percutaneous absorption improving agent. Since the release of the active substance is mainly controlled by the membrane, this transdermal therapeutic system is completely different from the active-substance-containing patch according to the present invention. In the patch described in said publication, the adhesive has the mere function of fastening the patch to the skin. The fact that it can contribute to the control of the active substance release is not its main function but merely a—probably even undesired—side effect. It is a so-called "pouch patch" since the active substance preparation is present in a pouch consisting of an impermeable backing layer and a membrane having an adhesive layer. As a consequence of its complicated structure, the production of this patch is very expensive since the individual components have to be produced separately and then joined in an additional step to form a patch.

EP 0 275 716 describes a two-layer transdermal therapeutic system—in contrast to the single-layer system according to the present invention—for the simultaneous administration of one or several estrogens which are dissolved or microdispersed in the polymeric layer. In addition to the active substances, the pressure sensitive adhesive layer comprises substances improving the transdermal absorption. Polymeric and pressure sensitive adhesive layer may consist of polyacrylates, silicones, or polyisobutylenes.

EP 0 072 251 describes a flexible, liquid-absorbing medicinal bandage. The substrate which is attached to the flexible backing layer consists of a hydrophilic matrix based on hydrophilic high-molecular polysaccharides and/or polyacrylic acid, polyacrylamide, ethylene-vinyl acetate-copolymers, and other polymers as well as of a liquid phase based on a solution or emulsion of carbohydrate, proteins, multivalent alcohols, and different active substances, amongst others hormones. The main feature of this invention is the moisture-absorbing adhesive.

EP 0 328 806 describes a transdermal therapeutic system without membrane; its matrix consists of a polyacrylate adhesive, a solvent, a penetration enhancer, and estrogens, the derivatives and combinations thereof.

WO 87/07 138 describes an estradiol patch based on a backing layer, an active-substance-containing matrix and a pressure sensitive adhesive covered with a removable protective layer. The matrix and pressure sensitive adhesive are manufactured in technologically very expensive operations by homogenizing, degassing, coating, drying, and separating. According to an embodiment, the backing layer has to be coated with a pressure sensitive adhesive, resulting in an additional operation. The individual parts are joined in a separate step. For this reason, the production of this patch is very expensive and complicated.

U.S. Pat. No. 4,624,665 describes systems comprising the active substance in microencapsulated form within the reservoir. The reservoir is embedded between the backing layer and a membrane. The outer edge of the system is provided with a pressure sensitive adhesive. The structure and the production of this system are very complicated since the active substance has to be microencapsulated and homogeneously distributed in a liquid phase which is then embedded between backing layer and membrane in additional process steps. In addition, this system must then be provided with an adhesive edge and covered with a protective layer.

Additionally, EP 0 186 019 describes active substance patches wherein water-swellable polymers are added to a rubber/adhesive-resin-mass and from which estradiol can be released. However, it turned out that the release of estradiol from these active substance patches is too low and does not meet the therapeutic requirements.

DE-OS 20 06 969 describes a patch or pressure sensitive adhesive dressing exhibiting system action; it contains contraceptive substances which are incorporated in the adhesive component or in the adhesive film. This publication discloses that the adhesive may be an acrylate.

DE-OS 39 33 460 describes an estrogen-containing active substance patch based on homo and/or copolymers with at least one derivative of the acrylic acid or with methacrylic acid in combination with water-swellable substances.

However, it turned out that pressure sensitive adhesive transdermal therapeutic matrix systems which comprise the active substance in a partially or completely dissolved form involve the potential risk that the active substance recrystallizes in the course of time. Thus the active substance release decreases and the estrogen-containing patch does no longer meet the therapeutic requirements.

Another drawback of systems according to the state of the art is the use of enhancers, this results in a fundamentally undesired additional skin affection including the risk of irritation. Additional disadvantages lie in the expensive construction of these systems (use of several active-substance-containing layers, use of controlling membranes), generally rendering the finished product unacceptable for the user.

BRIEF SUMMARY OF THE INVENTION

It is accordingly the object of the present invention to avoid the above disadvantages and to provide a stable, i.e., recrystallization-free, estrogen-containing patch or transdermal therapeutic system whose release does not change through storage, wherein the structure is to be designed as thin as possible, and during whose therapeutic application the skin—beyond the active substances estradiol and gestagen—is not treated with skin affecting substances (enhancers).

DETAILED DESCRIPTION OF THE INVENTION

Most surprisingly, it turned out that this object is achieved by the fact that the estrogen-containing pressure sensitive adhesive is mainly composed of esters of colophony.

In this connection it is of advantage that a styrene-isoprene block copolymer and hydrogenated resin acids or their derivatives are additionally used in the active layer which, for example, comprises a therapeutically required quantity of the active substances estradiol and levonorgestrel.

A combination of the two inactive ingredients, the styrene-isoprene block copolymer serving as cohesive component, and the hydrogenated resin acids or their derivatives serving as tackifying substances, not only results in a rubber adhesive with good tackiness and cohesiveness but also provides excellent biopharmaceutical properties, in particular good skin tolerance and permeation capability, and avoids recrystallization of the active substances.

Thus, the present invention relates to a transdermal therapeutic system for the controlled release of estradiol or its pharmaceutically acceptable derivatives alone or combined with gestagens, consisting of a backing layer, an active-substance-containing reservoir which is connected thereto and is produced by using pressure sensitive adhesives, and a removable protective layer, with the pressure sensitive adhesive comprising esters of colophony and inactive ingredients.

Examples of esters of colophony include, for example, methyl esters, the glycerol ester, the pentaerythritol ester, the pentaerythritol ester modified with maleic acid, the glycerol ester modified with maleic acid, and the triethylene glycol ester. The proportion of colophony esters in the estradiol-containing pressure sensitive adhesive amounts to 55–92%-wt., preferably 60–90%-wt., and most preferably 70–88%-wt. In addition, the pressure sensitive adhesive may comprise esters of hydrogenated colophony. Particularly preferred esters of colophony include the triethylene glycol ester, the glycerol ester, and the pentaerythritol ester of hydrogenated colophony.

According to another embodiment, the estradiol-containing pressure sensitive adhesive may additionally comprise polymers selected from the group consisting of styrene-butadiene-styrene block copolymers, styrene-isoprene-styrene block copolymers, styrene-ethylene-butylene-styrene block copolymers, ethylene-vinyl acetate copolymers, polyvinyl pyrrolidone, cellulose derivatives, and polymers based on acrylic acid and methacrylic acid derivatives. These polymers are contained in the estradiol-containing adhesive mass at a concentration of 6–25%-wt.

The reservoir of the estradiol-containing patch, wherein recrystallization does not occur, comprises estradiol and its pharmaceutically acceptable derivatives alone or in combination with gestagens at a total concentration of 2–15%-wt., namely at a molar ratio of 1:1 to 1:10. Generally, the estradiol is present in the active layer in an amount of 0.2 to 2% by weight, preferably between 0.7 and 1.4% by weight. The amount of levonorgestrel in the active layer is between 0.1 and 1.6% by weight. In addition, the levonorgestrel and/or the estradiol may be present partially in a suspension.

The estradiol-containing reservoir may comprise at least one component of the group including anti-ageing agents, plasticizers, antioxidants, and absorption improvers. Suitable plasticizers are known to those skilled in the art and are described, for example, in DE 37 43 946. Usually, the proportion of plasticizers in the estradiol-containing reservoir amounts to 0–5%-wt.

In addition, the active-substance-containing reservoir comprises anti-ageing agents at a concentration of 0–1%-wt. These are known to those skilled in the art and described, for example, in DE 37 43 946.

The estradiol-containing reservoir may either be produced from solution or from a melt.

In case the reservoir fails to exhibit sufficient self-tackiness to the skin, it may be provided with a pressure-sensitive adhesive layer or with a pressure-sensitive adhesive edge. This ensures that the transdermal patch adheres to the skin over the whole application period.

A particularly preferred construction of the transdermal estradiol-containing patch is the matrix system wherein, as is generally known, the matrix controls the active substance release which complies with the √t-law according to Higuchi. However, this is not to exclude the possibility that particular cases might require the membrane system. In this case, a membrane controlling the active substance release is located between the reservoir and the pressure sensitive adhesive layer.

The thickness of the transdermal patch depends on the therapeutic requirements and may be adapted accordingly. Usually, it ranges from 0.03–0.4 mm. The thickness of the active substance layer of the reservoir is between 30 and 300 μm, preferably between 70 and 120 μm.

In addition, a preferred application form is a monolithic matrix-type transdermal therapeutic system which consists of a backing layer substantially impermeable to the active substances, the actually active matrix layer (comprising the active substances and inactive ingredients according to the present invention) and of a removable protective layer.

The examples will show that these systems—although having a simpler construction and being made at lower expenditure than those according to the state of the art—have improved and more constant permeation characteristics for both active substances.

Surprisingly, it turned out that such a formulation which is composed of mainly lipophilic and comparatively low-diffusible polymers and resins results in human blood levels which cannot be obtained with systems according to the state of the art at a comparable low expenditure.

Until today, rubber adhesives have been regarded as being less suitable for the release of estradiol to the skin. For example, EP 0 186 01 9 describes the idea to use rubber adhesives (in this case by adding water-swellable substances), this is contradicted in EP 0 421 454 (p. 2, line 54 ff.): a sufficient release of estradiol is not given in the case of these low diffusible and only slightly soluble polymers.

Both substances which are essential to use according to the present invention, styrene-isoprene block copolymer and hydrogenated resin acids or their derivatives, have successfully been used for long as classic base materials of pressure sensitive adhesive patches and they have a good tolerance. The term "hydrogenated resin acids" means compounds derived from the natural product "colophony". Colophony is widely used as a mixture of native resin acids, above all in chemically modified form, in consumer goods, cosmetics, food packages, chewing gum, etc. it is the resinous residue of the raw product turpentine balsam remaining after distilling off turpentine oil; turpentine balsam originates from different pine trees in mainly subtropical-mediterranean climatic zones.

The crude product is a brittle, resinous mass softening at about 73–80° C. and having a density of about 1.07 g/ml. The modification of colophony for the purpose of using it in transdermal therapeutic systems serves to stabilize it against the influence of oxygen by hydrogenation and to improve the alkali stability by esterification. Hydrogenation and derivatization, if necessary, render the material more suitable for the intended purpose. Important esters which can be used for the purpose according to the present invention include, for example, glycerol esters, pentaerythritol esters, methyl esters, and other derivatives of hydrogenated colophony well tolerated by the skin.

Synthetic rubber polymers play an important role in the production of transdermal therapeutic systems and wound dressings. Their advantage lies in the fact that the mechanical properties of transdermal therapeutic systems are considerably improved. In this respect, the styrene-isoprene-styrene block copolymers have proved to be particularly suitable. By dividing the polymer chain into a middle block of still mobile long-chain polyisoprene units and the two polystyrene ends as "anchor points", a three-dimensional network is formed in the matrix, this ensures a substantially constant geometry, even during storage. In this connection it is not decisive which molecular weight or which ratio between the proportion of the styrene domains and the polyisoprene domains really exists. On the contrary, adjusting the correct tackiness and cohesion is the important factor. For example, an increased resin proportion results in an improved tackiness to the skin but also in a softer consistency of the matrix. In general, the proportion of the block copolymer will amount to about one third, the rest remaining after the active substance addition are biocompatible resin derivatives. Typically, the proportion of the styrene-isoprene block copolymer in the active layer amounts to 10–45% by weight, preferably 15–33% by weight.

Although a single-layer structure of the transdermal therapeutic system exhibits advantages because of the simple function, it is easily possible according to the present invention to provide such a matrix system, e.g., with a thin additional adhesive layer directed towards the skin. Also, for the purpose of obtaining an improved anchoring effect on the backing layer a thin pressure sensitive adhesive layer may be laminated. Such additional layers may consist of a rubber-resin-mixture but also, for example, of acrylic-ester-containing copolymers. They may be used even if not charged with active substances prior to lamination, since a diffusion compensation takes place during short-time intermediate storage of the complete laminate.

The transdermal patch is prepared by the following steps: kneading the mixture of esters of colophony at an elevated temperature until homogenization, incorporating active substance(s) and at least one polymer at the solution temperature, coating a removable protective layer with the active-substance-containing adhesive mass after homogenization, and laminating the backing layer.

The present invention will be illustrated in more detail by the following examples.

EXAMPLE 1

73.1 g triethylene glycol ester of hydrogenated colophony (Staybelite Ester 3E/by Hercules) and 9.8 g glycerol ester of hydrogenated colophony (Staybelite Ester 10E/by Hercules)

are mixed by kneading at 100° C. for 5 minutes. Then 2.5 g of estradiol are added. Kneading is continued for 30 minutes. After heating to 140° C., 14.6 g ethyl cellulose N50NF (by Hercules) are added in portions, and then kneading is continued for 2.5 hours.

In a hot melt coating line (die coating system) the active-substance-containing adhesive mass thus obtained is coated onto a removable protective layer (Hostaphan RN 100, coated on one side with silicone—by Kalle) in such a manner that an active-substance-containing reservoir having a mass per unit area of 80 g/m$^2$ results. An impermeable backing layer (polyester sheet, thickness 15 μm) is laminated on this reservoir. Subsequently, active substance patches of 16 cm$^2$ are punched.

EXAMPLE 2

The manufacture is in accordance with Example 1, with the plasticizer being kneaded together with the two Staybelite esters 3E and 10E.

EXAMPLES 3–9

Manufacture according to Example 1, however with the raw products and quantities as listed in Table 1 (manufacturing formula).

Analytic procedure

The active substance release of the transdermal patches having a size of 16 cm² is determined according to the Rotating bottle-method described in U.S. Pat. No. XXII in 0.9% salt solution at 37° C.

To measure the mice skin penetration, the skin of hairless mice is placed in the Franz-cell. An estradiol-containing patch having an area of 2.54 cm² is stuck onto the skin, and the active substance release is measured at 37° C. (acceptor medium: 0.9% saline). (literature: Umesh V. Banakar Pharmaceutical dissolution testing (1st edition—1991)).

The recrystallization testing is carried out visually against the light.

The results are listed in Table 2.

TABLE 1 manufacturing formula (indications in g)

| Ex. | Ethyl cellulose N50NF | Staybelite Ester 3E | Plasticizer 10E | Miglyol 812 | Estradiol | Antioxidants |
|---|---|---|---|---|---|---|
| 1 | 14.6 | 73.1 | 9.8 | — | 2.5 | |
| 2 | 14.3 | 71.6 | 9.6 | 2.0 | 2.5 | |
| 3 | 10.1 | 75.4 | 10.0 | 2.0 | 2.5 | |
| 4 | 7.7 | 77.5 | 10.3 | 2.0 | 2.5 | |
| 5 | 14.3 | 71.6 | 9.5 | 2.0 | 2.5 | 0.1 BHT |
| 6 | 14.3 | 71.6 | 9.5 | 2.0 | 2.5 | 0.1 BHA |
| 7 | 14.3 | 71.6 | 9.5 | 2.0 | 2.5 | 0.1 BHT:BHA = 1:1 |
| 8 | 14.3 | 71.6 | 9.6 | 2.0 isopropyl palmitate | 2.5 | |
| 9 | 14.3 | 71.6 | 9.5 (x) | 2.0 | 2.5 | |

BHT = butyl hydroxytoluene
BHA = butyl hydroxyanisole
(x) = Foral 105 (pentaerythritol ester of hydrogenated colophony)

TABLE 2

Results of Analysis

| Ex. | Estradiol content μg/16 cm² | in-vitro-release μg/16 cm² · 24 h | Mice skin penetration μg/16 cm² · 24 h | Recrystallization |
|---|---|---|---|---|
| 1 | 3200 | 614 | 225 | no |
| 2 | 3200 | 1240 | 300 | " |
| 3 | 3200 | 722 | 235 | " |
| 4 | 3200 | 713 | 268 | " |
| 5 | 3200 | 624 | 228 | " |
| 6 | 3200 | 624 | 249 | " |
| 7 | 3200 | 620 | 205 | " |
| 8 | 3200 | 686 | 232 | " |
| 9 acc. to DE 3933460 | 3200 | 2400 | 125 | considerable |

The Table shows that a considerably improved penetration through the mice skin is obtained, as evidenced by the comparative example under DE 3933460. Analogously, there is no recrystallization in the Examples according to the present invention.

EXAMPLE 10

1.0 g 17-β-estradiol
1.3 g levonorgestrel
60.0 g Cariflex®TR 1107 (styrene-isoprene-styrene block copolymer), 138.0 g Foral®85 (thermoplastic ester resin of colophony derivatives)
200.0 g benzine (boiling range 80–100° C.)
are stirred in a cylindrical glass vessel at room temperature until an even suspension results and then coated on a siliconized polyester sheet of 100 μm thickness in a continuous coating line in such a manner that a layer thickness of 110 g/m² (relative to the solvent-free portion) results. The coating is dried at 40° C., 60° C., 75° C., and 125° C. for 3 minutes each. A polyester sheet of 12 μm thickness is immediately placed on the dry layer without air-bubbles under roll pressure (laminated). Transdermal systems of 20 cm² are obtained by punching using a wad punch.

EXAMPLE 11

Manufacture of a system according to the invention
1.5 g 17-β-estradiol
1.5 g levonorgestrel
70.0 g styrene-isoprene-styrene block copolymer
150.0 g thermoplastic ester resin of colophony derivatives
are melted and combined by kneading in a heatable kneader at 150° C. under nitrogen within 24 h. On a continuous coating line, a polyester sheet of 19 μm thickness is coated with the melt at a layer thickness of 100 μm. This may be effected at 140° C. in a hot melt coater, or at about 80–100° C. by means of an extruder. Subsequently, a siliconized polyester sheet of 150 μm thickness, precoated with 20 g/m² of an acrylic ester copolymer (Durotak®280–2516), is placed on the dried layer (laminated) without air-bubbles and under roll pressure. Transdermal systems of 20 cm² are obtained by punching using a wad punch.

What is claimed is:

1. A transdermal therapeutic system for the controlled release of estradiol or a pharmaceutically acceptable derivative thereof, said system comprising a backing layer; an active-substance-containing reservoir which is bonded to the backing layer and which comprises pressure sensitive adhesive and estradiol or a pharmaceutically acceptable derivative thereof combined with a gestagen; and a removable protective layer, wherein the pressure sensitive adhesive comprises (a) a styrene-isoprene block copolymer, and
(b) a hydrogenated resin acid or its derivatives in an amount of 55–92% wt.

2. The transdermal therapeutic system according to claim 1, wherein the pressure sensitive adhesive comprises the hydrogenated resin acid or its derivatives in an amount of 60–90% wt.

3. The transdermal therapeutic system according to claim 1, wherein the pressure sensitive adhesive comprises the hydrogenated resin acid or its derivatives in an amount of 70–88% wt.

4. The transdermal therapeutic system according to claim 1, wherein the active-substance-containing reservoir comprises the active substances estradiol and levonorgestrel, as the gestagen, wherein the polymer is styrene-isoprene block copolymer.

5. The transdermal therapeutic system according to claim 1, wherein the derivatives of the hydrogenated acid resins are esters selected from the group consisting of methyl ester, glycerol ester, pentaerythritol ester, pentaerythritol ester modified with maleic add, glycerol ester modified with maleic acid, and triethylene glycol ester.

6. The transdermal therapeutic system according to claim 1, wherein the concentration of estradiol or its pharmaceutically acceptable derivatives in the active-substance-containing reservoir is between 0.2 and 2 percent by weight.

7. The transdermal therapeutic system according to claim 6, wherein the concentration of the estradiol or its pharmaceutically acceptable derivative in the active-substance-containing reservoir is between 0.7 and 1.4 percent by weight.

8. The transdermal therapeutic system according to claim 4, wherein the concentration of levonorgestrel in the active-substance-containing reservoir is between 0.1 and 1.6 percent by weight.

9. The transdermal therapeutic system according to claim 1, wherein the active-substance-containing reservoir has a layer thickness between 30 and 300 µm.

10. The transdermal therapeutic system according to claim 9, wherein the thickness of the active-substance-containing reservoir is between 70 and 120 µm.

11. The transdermal therapeutic system according to claim 4, wherein the amount of styrene-isoprene block copolymer in the active-substance-containing reservoir is 10 to 45 percent by weight.

12. The transdermal therapeutic system according to claim 11, wherein the amount of the styrene-isoprene block copolymer in the active-substance-containing reservoir is 15 to 33 percent by weight.

13. The transdermal therapeutic system according to claim 1, wherein at least one of the active substances, levonorgestrel as the gestagen or estradiol or its pharmaceutically acceptable derivative is present partially in suspension.

14. The transdermal therapeutic system according to claim 11, wherein part of the estradiol is present in the form of estradiol crystals, with the estradiol crystals substantially consisting of precipitated estradiol anhydrate.

15. The transdermal therapeutic system according to claim 11, wherein the hydrogenated resin acid or its derivative comprises esters of hydrogenated colophony.

16. The transdermal therapeutic system according to claim 1, wherein the reservoir comprises estradiol or a pharmaceutically acceptable derivative of estradiol in combination with a gestagen in a concentration totaling 2–15% wt., wherein the molar ratio of estradiol or its pharmaceutically acceptable derivative to the gestagen is 1:1 to 1:10.

17. The transdermal therapeutic system according to claim 1, wherein the reservoir comprises at least one component selected from the group consisting of an anti-ageing agent, a plasticizer, an antioxidant, and an absorption improver, with the plasticizer being contained in a concentration of 0–5% wt. and the anti-ageing agent being contained in a concentration of 0.1% wt.

18. The transdermal therapeutic system according to claim 1, wherein the pressure sensitive adhesive is a solvent-based pressure sensitive adhesive.

19. The transdermal therapeutic system according to claim 1, wherein the pressure sensitive adhesive is a hot-melt pressure sensitive adhesive.

20. The transdermal therapeutic system according to claim 11, wherein the reservoir consists of a plurality of layers.

21. The transdermal therapeutic system according to claim 1, wherein the reservoir is provided with an additional pressure sensitive adhesive layer or with a pressure sensitive adhesive edge.

22. The transdermal therapeutic system according to claim 21, wherein a membrane which controls the active substance release is located between the reservoir and the additional pressure sensitive adhesive layer.

23. A process for the production of a transdermal therapeutic system as defined in claim 11, which comprises:

kneading a mixture of a hydrogenated resin acid or its derivatives at an elevated temperature until homogenization is achieved, incorporating the active substances and the polymer at the solution temperature, coating a removable protective layer with the resulting active-substance-containing adhesive mass after homogenization, and laminating a backing layer.

24. A method for the therapeutic treatment of a human or an animal which comprises applying to the skin of said human or animal a transdermal therapeutic system as defined in claim 11, in the form of a patch.

* * * * *